US00PP17465P2

(12) United States Plant Patent
Elsner

(10) Patent No.: US PP17,465 P2
(45) Date of Patent: Mar. 6, 2007

(54) **VARIETY OF *GERANIUM* NAMED 'PENDEC'**

(50) Latin Name: *Pelargonium×peltatum*
Varietal Denomination: Pendec

(75) Inventor: Wilhelm Elsner, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 1220 days.

(21) Appl. No.: 09/664,247

(22) Filed: Sep. 18, 2000

(51) Int. Cl.
*A01H 5/00* (2006.01)

(52) U.S. Cl. ..... Plt./332; Plt./324; Plt./328
(58) Field of Classification Search ..... Plt./324, Plt./328, 332
See application file for complete search history.

(56) References Cited

PUBLICATIONS

Cooper, I.P., "Biotechnology and the Law", 2000 Revision, vol. 2, Clark Boardman Callaghan, Section 8.05.*

UPOV–ROM GTITM Computer Database, 2001/02, GTI Jouve Retrieval Software, citation for 'Pendec'.*

Halpin, A.; "Horticulture—Gardner's Desk Reference," Macmillan; 1996, pp. 82–85.*

UPOV ROM GTITM, Plant Variety Database, 2005/03, GTI Retrieval Software, citation for geranium 'Pendec'.*

Council Regulation (EC) No. 2100/94 on Community plant variety rights, Jul. 27, 1994.*

Webster's New World Dictionary of the American Language, Second College Edition, p. 1112 (The World Publishing Co. 1972).*

* cited by examiner

*Primary Examiner*—Anne Marie Grunberg
*Assistant Examiner*—S. B. McCormick-Ewoldt
(74) *Attorney, Agent, or Firm*—The Webb Law Firm

(57) ABSTRACT

A new and distinct variety of *geranium* having flowers with a pinkish-white color above medium green foliage and a yellow stem. It provides superb cuttings and performs well in a hanging basket. The blooms hold up well when exposed to direct sunlight.

1 Drawing Sheet

BACKGROUND OF THE INVENTION

This discovery relates to a new and distinct cultivar of *Pelargonium×peltatum* known by the varietal name of 'Pendec.' The seedling from the present variety is a spontaneous mutation of 'Pendresd' (patent pending). The new variety was discovered in France on Jun. 22, 1996. The new variety was first asexually reproduced by cuttings at Elsner pac Jungpflanzen in Dresden, Germany on Oct. 15, 1996. It has been found to retain its distinctive characteristics through successive propagations.

The new cultivar has similar flower color and form to 'Pendresd' but is a shorter internode length and has yellower stems than 'Pendresd.'

The cultivar, when grown in a glass greenhouse at high humidity using natural light and 18° C. night and 20° C. day, has a response time of ten weeks from a rooted cutting to flowering in a 10 cm pot. The response time was determined on plants grown in peat substrates.

DESCRIPTION OF THE DRAWING

The accompanying photographic drawing illustrates the new variety, with the color being as nearly true as is possible with color illustrations of this type.

DESCRIPTION OF THE PLANT

The following detailed descriptions set forth the characteristics of the new variety. The data which define these characteristics were collected from asexual reproductions carried out at Elsner pac Jungpflanzen, Kipsdorfer Strasse 146, D-01279, Dresden, Germany. The color readings were taken in natural light. Color references are primarily to The Royal Horticultural Society Colour Chart.

THE PLANT

Classification:
- *Botanical.*—*Pelargonium×pelatatum.*
- *Varietal.*—Ivy- *geranium* named 'Pendec'.
- *Commercial.*—Ivy- *geranium* named 'Ville de Dresden, Deror'.

Form: Cascading mound.
Height: Up to 70–80 cm.
Growth: Hanging, very high degree of branching.
Strength: No artificial support required.
Foliage: Alternate leaf attachment.
Rooting time: 3.5–4 weeks.
Leaves:
- *Size.*—Length: 5.5 cm. Width: 4–5 cm.
- *Shape.*—Ivy-shaped.
- *Margin.*—Pedately lobed with serrations.
- *Color.*—Top surface: Green Group 137A. Bottom surface: Green Group 138A. Zone: Green Group 139A.
- *Ribs and veins.*—Venation: Palmate. Color: Green Group 144A on lower surface.

Petioles:
- *Length.*—Up to 2 cm.
- *Color.*—Yellow-green Group 145C.

Stem:
*Color.*—Yellow Group 150C.
*Internode length.*—2–4 cm.

THE BUD

Cluster:
*Shape.*—Nearly in one line.
*Size.*—Approximately 2.5 cm diameter.
*Number of buds per cluster.*—Approximately seven.
*Individual buds* (*when showing five leaf pairs*).—Shape: Elongated. Size: 3 mm wide, up to 1 cm long.

INFLORESCENCE

Blooming habit: Windmill-shaped.
Borne: Umbel, florets on pedicel, pedicel on peduncle.
Size of umbel: 7–9 cm in diameter.
Open florets:
*Form.*—Single, free spaces between petals, approximately seven florets per umbel.
*Size.*—3 cm wide, 4.5 cm high, 2 cm deep.
*Petals.*—Color: Top surface: Red Group 56D. Bottom surface: White Group 155D. Shape: Spoon-shaped. Size: Upper: 1.5 cm wide, 27 cm long. Lower: 1.1 cm wide, 2.2 cm long. Texture and appearance: Smooth.
Tonality from a distance: White pearls over green foliage.
Petaloids: None.
Pedicel:
*Length.*—2.5–3 cm.
*Color.*—Yellow Group 145C and Red Group 60B.
Peduncle:
*Length.*—4–6 cm.
*Color.*—Yellow-green Group 145C.

Disease and pest resistance: No unusual susceptibility and to disease or pests seen to date.
Lasting quality: Flowers hold 8–10 days, depending on weather conditions; resistant in rain.

REPRODUCTIVE ORGANS

Stamens:
*Anthers.*—Up to 3 mm long.
*Filaments.*—Length: Up to 5 mm. Color: Yellow Group 11D.
*Pollen.*—Bright yellow.
Pistils:
*Number.*—1;5 parted.
*Length.*—1–1.2 cm.
*Stigma.*—Number: 1;5 parted. Color: Red-purple Group 59D.
*Style.*—Color: White. Length: 5 mm.
*Ovaries.*—Color: Green Group 141C. Size: 5 mm long; 2 mm wide. Pubescense: Some present.
Fruit: None observed.

GENERAL CHARACTERISTICS

The new *geranium* variety provides a flower color similar to its parent, 'Pendresd,' with a shorter internode length and a different color stem (yellow) using minimal fertilization. It is rich flowering, well-branched, hangs well, and has a stable flower color under intense sunlight. These properties provide an impressive appearance from a distance. Cutting production and wind resistance are excellent.

I claim:

1. A new and distinct variety of *geranium* plant named 'Pendec' as described and illustrated herein.

* * * * *

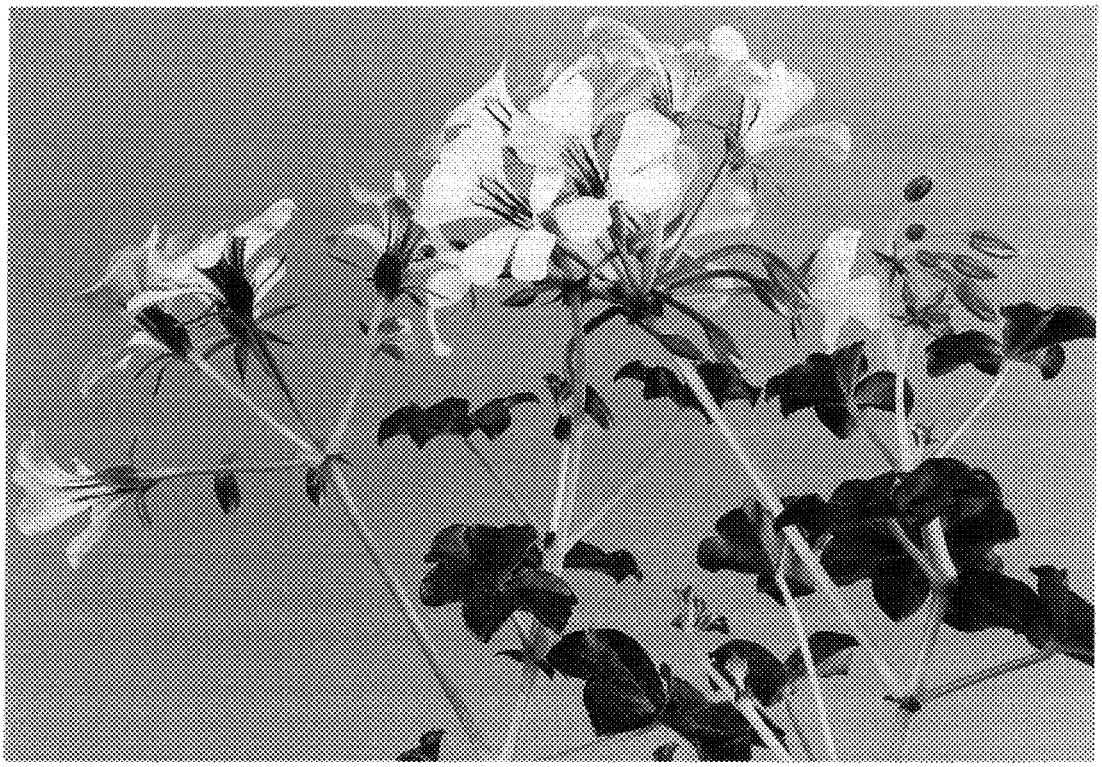

UNITED STATES PATENT AND TRADEMARK OFFICE

CERTIFICATE OF CORRECTION

PATENT NO. : PP 17,465 P2
APPLICATION NO. : 09/664247
DATED : March 6, 2007
INVENTOR(S) : Wilhelm Elsner It is certified that error appears in the above-identified patent and that said Letters Patent is hereby corrected as shown below:

Column 1, Line 14, after "Pendresd.", insert the following: -- 'Pendresd' is a single flowering peltatum hybrid with white-nacreous and zygomorph flowers. The two upper petals are wider and overlapping with burgundy colored markings. The three more narrow lower petals are not overlapping and do not have any markings. --

Column 2, Lines 2-3, delete "at Elsner pac Jungpflanzen, Kipsdorfer Strasse 145, D-01279, Dresden, Germany." and insert therefor -- in Dresden, Germany. Observations of the new variety were taken 8 months after rooted cuttings were planted. --

Column 2, after Line 23, "*Margin*.—Pedately lobed with serrations.", insert the following: -- Texture: Smooth --

Column 2, after Line 29, "Color.—Yellow-green Group 245C.", insert the following:
-- Diameter: 1.5-2.0 mm. --

Column 3, after Line 3, "*Internode length*.—2—4 cm.", insert the following:
-- Length: 35 cm.
Diameter: 3.0-3.5 mm. --

Column 3, in the section under "Open florets: in the *Petals* section, after "White Group 155D'", insert the following: --with streaks of Red-Purple Group 64B. --

UNITED STATES PATENT AND TRADEMARK OFFICE

CERTIFICATE OF CORRECTION

PATENT NO. : PP 17,465 P2
APPLICATION NO. : 09/664247
DATED : March 6, 2007
INVENTOR(S) : Wilhelm Elsner It is certified that error appears in the above-identified patent and that said Letters Patent is hereby corrected as shown below:

Column 3, after "Tonality from a distance: White pearls over green foliage.", insert the following:

-- Sepals:

| | |
|---|---|
| Length: | 1.2 cm. |
| Width: | 0.2-0.5 cm. |
| Color: | Yellow-Green Group 144B. |
| Texture: | Hairy. |
| Average number: | 5. -- |

Signed and Sealed this

Twenty-first Day of August, 2007

JON W. DUDAS
*Director of the United States Patent and Trademark Office*